(12) United States Patent
Grubbs et al.

(10) Patent No.: US 6,613,910 B2
(45) Date of Patent: Sep. 2, 2003

(54) ONE-POT SYNTHESIS OF GROUP 8 TRANSITION METAL CARBENE COMPLEXES USEFUL AS OLEFIN METATHESIS CATALYSTS

(75) Inventors: Robert H. Grubbs, South Pasadena, CA (US); John P. Morgan, South Pasadena, CA (US); Diego Benitez, Pasadena, CA (US); Janis Louie, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/115,581

(22) Filed: Apr. 2, 2002

(65) Prior Publication Data

US 2003/0100782 A1 May 29, 2003

Related U.S. Application Data

(60) Provisional application No. 60/309,806, filed on Aug. 1, 2001, and provisional application No. 60/281,046, filed on Apr. 2, 2001.

(51) Int. Cl.$^7$ ............... C07F 15/00; C07F 9/02; C07D 233/00
(52) U.S. Cl. .............. 548/103; 556/21; 556/23; 556/136; 502/152; 548/300.1
(58) Field of Search ............. 556/21, 23, 136; 502/152; 548/103, 300.1

(56) References Cited

U.S. PATENT DOCUMENTS

| 5,917,071 A | 6/1999 | Grubbs et al. ............ 556/21 |
| 6,048,993 A | 4/2000 | Grubbs et al. ............ 556/21 |
| 2002/0022733 A1 | 2/2002 | Grubbs et al. ............ 556/136 |

OTHER PUBLICATIONS

Arduengo et al. (1999), "C–H Insertion Reactions of Nucleophilic Carbenes," *Helvetica Chimica Acta* 82:2348–2364.

Huang et al. (1999), "Olefin Metathesis–Active Ruthenium Complexes Bearing a Nucleophilic Carbene Ligand," *J. Am. Chem. Soc.* 121(12):2674–2678.

Jafarpour et al. (2000), "Simple and Convenient Synthetic Procedure Leading to Ruthenium Olefin Metathesis Catalysts Bearing the N,N'-Bis(mesityl)imidazol–2–ylidene (IMes) Ligand," *Organometallics* 19(11):2055–2057.

Jafarpour et al. (2002), "Improved One–Pot Synthesis of Second–Generation Ruthenium Olefin Metathesis Catalysts," *Organometallics* 21(2):442–444.

Scholl et al. (1999), "Increased Ring Closing Metathesis Activity of Ruthenium–Based Olefin Metathesis Catalysts Coordinated with Imidazolin–2–ylidene Ligands," *Tetrahedron Letters* 40:2247–2250.

Scholl et al. (1999), "Synthesis and Activity of a New Generation of Ruthenium–Based Olefin Metathesis Catalysts Coordinated with 1,3–Dimesityl–4,5–dihydroimidazol–2–ylidene Ligands," *Organic Letters* 1(6):953–956.

Trnka et al. (2001), "The Development of $L_2X_2Ru$=CHR Olefin Metathesis Catalysts: An Organometallic Success Story," *Accounts of Chemical Research* 34(1):18–29.

van der Schaaf et al. (2000), "A 14–Electron Ruthenium Hydride: The Key Intermediate in the Synthesis of Ruthenium Carbene Complexes; X–ray Structure of [RuHCl(P-Pr$^{i3}$)$_2$]," *Chem. Commun.*, pp. 1045–1046.

Weskamp et al. (1998), "A Novel Class of Ruthenium Catalysts for Olefin Metathesis," *Angew. Chem. Int. Ed.* 37(18):2490–2493.

Wilhelm et al. (1997), "Reactivity of $Ru(H)(H_2)Cl(PCy_3)_2$ with Propargyl and Vinyl Chlorides: New Methodology to Give Metathesis–Active Ruthenium Carbenes," *Organometallics* 16(18):3867–3869.

Herrmann et al. (1998), "A Novel Class of Ruthenium Catalysts of Olefin Metathesis," *The Royal Society of Chemistry, Dalton Division, 11$^{th}$ International Symposium on Homogeneous Catalysis*, University of St. Andrews, Scotland, United Kingdom.

Schwab et al. (1996), "Synthesis and Applications of $RuCl_2$(=CHR')(PR$_3$)$_2$: The Influence of the Alkylidene Moiety on Metathesis Activity," *J. Am. Chem. Soc.* 118(1):100–110.

*Primary Examiner*—Porfirio Nazario-Gonzalez
(74) *Attorney, Agent, or Firm*—Dianne E. Reed; Reed & Eberle LLP

(57) ABSTRACT

The invention provides a novel method for synthesizing transition metal carbene complexes useful as olefin metathesis catalysts. The method is a convenient one-pot synthesis in which transition metal carbenes are prepared in high yield from readily available starting materials via a dihydrogen complex containing two different anionic ligands, preferably a phosphine and a heteroatom-stabilized carbene. The invention additionally provides a method for synthesizing precursors to carbene ligands useful, inter alia, in the aforementioned one-pot synthesis. The precursors are in the form of trichloromethyl adducts of the formula $L^1$-$CCl_3$, where $L^1$ is a heteroatom-stabilized carbene ligand, and are prepared by contacting an unsaturated, ionized analog of L-$CCl_3$ with a non-nucleophilic base in the presence of chloroform.

27 Claims, No Drawings

ONE-POT SYNTHESIS OF GROUP 8 TRANSITION METAL CARBENE COMPLEXES USEFUL AS OLEFIN METATHESIS CATALYSTS

CROSS-REFERENCE TO RELATED APPLICATIONS

This application claims priority under 35 U.S.C. §119(e)(1) to the following provisional U.S. patent applications: Ser. No. 60/281,046, filed Apr. 2, 2001; and Ser. No. 60/309,806, filed Aug. 1, 2001. The disclosures of the aforementioned applications are incorporated by reference in their entireties.

ACKNOWLEDGEMENT OF GOVERNMENT SUPPORT

This invention was developed with U.S. Government support under grant numbers 2 R01 GM31332 and 3 R01 GM31332-16 awarded by the National Institutes of Health, and under grant number CHE 9809856 awarded by the National Science Foundation. The Government has certain rights in the invention.

TECHNICAL FIELD

This invention relates generally to a method for synthesizing Group 8 transition metal carbene complexes useful as olefin metathesis catalysts, and more particularly relates to a novel one-pot synthesis of mixed ligand transition metal carbene catalysts that contain a heteroatom-stabilized carbene ligand, e.g., an imidazolylidene ligand. The invention also pertains to a method for synthesizing a precursor to heteroatom-stabilized carbene ligands, particularly 1,3-disubstituted-2-trichloromethyl-5-dihydroimidazolidene.

BACKGROUND OF THE INVENTION

To the synthetic organic or polymer chemist, simple methods for forming carbon-carbon bonds are extremely important and valuable tools. One method of C—C bond formation that has proved particularly useful is transition-metal catalyzed olefin metathesis. "Olefin metathesis," as is understood in the art, refers to the metal-catalyzed redistribution of carbon-carbon bonds. See Trnka and Grubbs (2001) *Acc. Chem. Res.* 34:18–29. Over two decades of intensive research effort has culminated in the discovery of well-defined ruthenium and osmium carbenes that are highly active olefin metathesis catalysts and stable in the presence of a variety of functional groups.

These ruthenium and osmium carbene complexes have been described in U.S. Pat. Nos. 5,312,940, 5,342,909, 5,831,108, 5,969,170, 6,111,121, and 6,211,391 to Grubbs et al., assigned to the California Institute of Technology. The ruthenium and osmium carbene complexes disclosed in these patents all possess metal centers that are formally in the +2 oxidation state, have an electron count of 16, and are penta-coordinated. These catalysts are of the general formula (I):

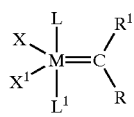

where M is a Group 8 transition metal such as ruthenium or osmium, X and X' are anionic ligands, L and L' are neutral electron donors, and R and R' are specific substituents, e.g., one may be H and the other may be a substituted or unsubstituted hydrocarbyl group such as phenyl or C═C(CH$_3$)$_2$. Such complexes have been disclosed as useful in catalyzing a variety of olefin metathesis reactions, including ring opening metathesis polymerization ("ROMP"), ring closing metathesis ("RCM"), acyclic diene metathesis polymerization ("ADMET"), ring-opening metathesis ("ROM"), and cross-metathesis ("CM" or "XMET") reactions.

For the most part, such metathesis catalysts have been prepared with phosphine ligands, e.g., triphenylphosphine or dimethylphenylphospine, exemplified by the well-defined, metathesis-active ruthenium alkylidene complexes (II) and (III):

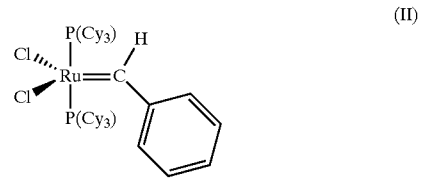

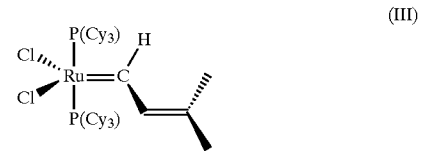

wherein "Cy" is a cycloalkyl group such as cyclohexyl or cyclopentyl. See U.S. Pat. No. 5,917,071 to Grubbs et al. and Trnka and Grubbs, cited supra. These compounds are highly reactive catalysts useful for catalyzing a variety of olefin metathesis reactions, and are tolerant of many different functional groups. However, as has been recognized by those in the field, the compounds display low thermal stability, decomposing at relatively low temperatures. Jafarpour and Nolan (2000) *Organometallics* 19(11):2055–2057.

Recently, however, significant interest has focused on the use of N-heterocyclic carbene ligands as superior alternatives to phosphines. See, e.g., Trnka and Grubbs, supra; Bourissou et al. (2000) *Chem. Rev.* 100:39–91; Scholl et al. (1999) *Tetraheron Lett.* 40:2247–2250; Scholl et al. (1999) *Organic Lett.* 1(6):953–956; and Huang et al. (1999) *J. Am. Chem. Soc.* 121:2674–2678. N-heterocyclic carbene ligands offer many advantages, including readily tunable steric bulk, vastly increased electron donor character, and compatibility with a variety of metal species. In addition, replacement of one of the phosphine ligands in these complexes significantly improves thermal stability. The vast majority of research on these carbene ligands has focused on their generation and isolation, a feat finally accomplished by Arduengo and coworkers within the last ten years (see, e.g., Arduengo et al. (1999) *Acc. Chem. Res.* 32:913–921). Representative of these second generation catalysts are the four ruthenium complexes (IVA), (IVB), (VA) and (VB):

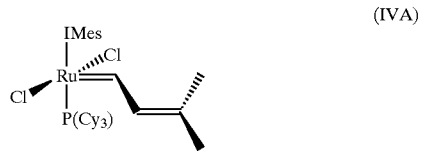

-continued

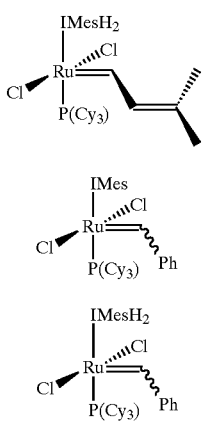

(IVB)

(VA)

(VB)

In the above structures, Cy is as defined previously, "IMes" represents 1,3-dimesityl-imidazol-2-ylidene IMes:

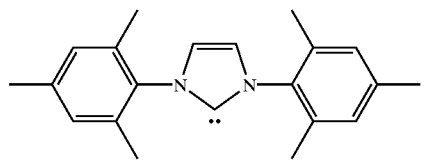

and "IMesH$_2$" represents 1,3-dimesityl-4,5-dihydroimidazol-2-ylidene

IMesH$_2$:

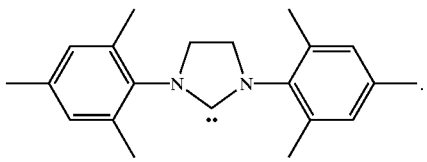

These transition metal carbene complexes, particularly those containing a ligand having the 4,5-dihydroimidazol-2-ylidene structure, such as in IMesH$_2$, have been found to address a number of previously unsolved problems in olefin metathesis reactions, particularly cross-metathesis reactions. These problems span a variety of reactions and starting materials.

Previously, synthetic routes to such complexes have involved multiple steps and have required air- and moisture-sensitive carbene precursors as starting materials. Such methods are described, for example, by Scholl et al. (1999) *Tet. Lett.* 40:2247–2250, Kingsbury et al. (1999) *J. Am. Chem. Soc.* 121:791–799, and Huang et al. (1999), cited supra. There is, accordingly, a need in the art for a practical, convenient synthesis of catalysts such as (IVA), (IVB), (V), and (VB), possessing an N-heterocyclic carbene ligand, which provides the desired complexes in high yield using air- and moisture-stable precursors. It would also be desirable if such a synthesis were broadly applicable in the manufacture of other mixed ligand metal alkylidenes as well as related complexes, e.g., mixed ligand metal vinylidenes. The present invention is, in part, directed to such a synthesis.

The invention additionally addresses the problems those working in the field have encountered with synthesis of N-heterocyclic carbene reactants used to prepare catalysts such as (VA) and (VB). Early efforts sought to generate free N-heterocyclic carbenes from electron-rich olefins known as enetetraamines (Scheme 1, reaction (a)). Unfortunately, these olefins are typically only slightly more air- and light-stable than their constituent carbenes; they often undergo rapid oxidation in solution. Even when these olefins are oxidatively stable, their thermal cleavage remains debatable, thereby preventing these olefins from serving as protected carbenes. As an additional drawback, these olefins cleave only at extremely high temperatures that are often incompatible with sensitive metal species. The electron-rich nature of enetetramines also led to the investigation of their cleavage by reaction with electrophiles (Scheme 1(b)). Unfortunately, such reactions are generally unsuitable for use in organometallic synthesis, given the possibility of diverse problems. For example, many nucleophilic metal species will not tolerate strong electrophiles (such as $CO_2$ and $SO_2$) that are required in the cleavage reactions. More importantly, the mechanisms of these electrophilic reactions remain poorly understood; the choice of optimal electrophile remains unclear. With these observations, the "electrophilic" route appears ill-suited for a general synthesis of N-heterocyclic carbene-coordinated metal species.

Scheme 1
Common base-free synthetic routes to heterocyclic carbones.

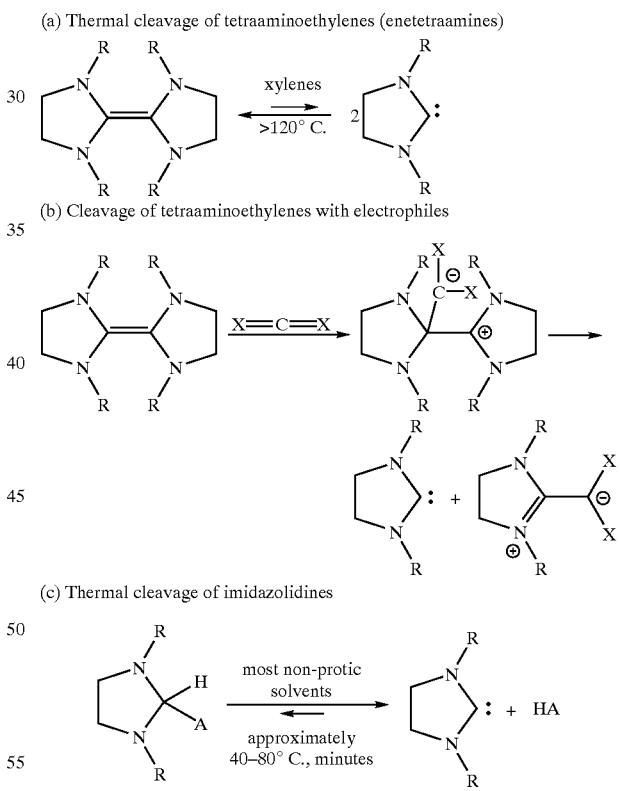

An improved method involves the formation of carbene "adducts" by thermal ejection of a leaving group, as illustrated in Scheme 1, reaction (c). In this scheme, the R groups will typically be aryl substituents (e.g., mesitylene) and an optimal "A" group is $CCl_3$. Such a synthesis is described by Wanzlick et al. (1961) *Chemiche Berichte* 94:2389–2393, and involves direct condensation of N,N'-diaryl-1,2-diamines with chloral (trichloroacetaldehyde), an impractical route since chloral is subject to distribution regulations, preventing its widespread availability.

An improved method for preparing N-heterocyclic carbene reactants useful, inter alia, in the synthesis of metal carbene complexes, would involve readily available reagents, straightforward reaction conditions (e.g., involving non-dry, non-degassed solvents), with generation of any toxic and/or reactive by-products minimized.

SUMMARY OF THE INVENTION

The present invention is addressed to the aforementioned needs in the art, and provides new synthetic routes to metal carbene catalysts, particularly Group 8 transition metal complexes containing a heteroatom-stabilized carbene ligand. Such catalysts, as explained above, are highly active catalysts of olefin metathesis reactions, and are advantageous in many respects. The present synthetic methods, which are "one-pot" syntheses, provide straightforward and convenient routes to obtaining the aforementioned catalysts in high yield using air- and moisture-stable precursors. The methods are also versatile insofar as they are generally applicable in the preparation of a variety of mixed ligand metal carbene complexes.

In one aspect of the present invention, a one-pot synthesis is provided for preparing Group 8 transition metal alkylidene complexes of the formula (V):

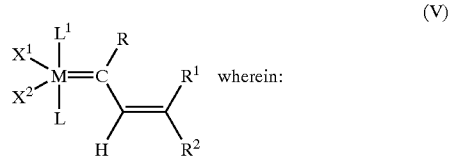

(V)

wherein:

M is a Group 8 transition metal, particularly Ru or Os;

$X^1$ and $X^2$ may be the same or different, and are anionic ligands or polymers;

R, $R^1$ and $R^2$ are independently selected from the group consisting of hydrogen, hydrocarbyl, substituted hydrocarbyl, heteroatom-containing hydrocarbyl, substituted heteroatom-containing hydrocarbyl, and -$(Z)_n$-Fn where n is zero or 1, Z is a hydrocarbylene, substituted hydrocarbylene and/or heteroatom-containing hydrocarbylene linkage, and Fn is a functional group;

L is any neutral electron donor ligand; and $L^1$ is a neutral electron donor ligand having the structure of formula (VI):

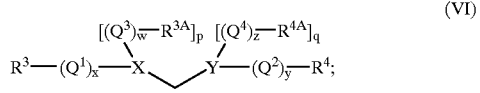

(VI)

X and Y are heteroatoms selected from N, O, S, and P;

p is zero when X is O or S, and is 1 when X is N or P;

q is zero when Y is O or S, and is 1 when Y is N or P;

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—;

w, x, y and z are independently zero or 1; and $R^3$, $R^{3A}$, $R^4$, and $R^{4A}$ are independently selected from the group consisting of hydrogen, hydrocarbyl, substituted hydrocarbyl, heteroatom-containing hydrocarbyl, and substituted heteroatom-containing hydrocarbyl, wherein any two or more of $X^1$, $X^2$, L, R, $R^1$, $R^2$, $R^3$, $R^{3A}$, $R^4$, and $R^{4A}$ can be taken together to form a chelating multidentate ligand.

The method involves, initially, combining a metal complex $ML^3(X^1)_2$, where M and $X^1$ are as defined above and $L^3$ is a bidentate organic ligand, with: (a) a salt or adduct of $L^1$, which serves as a precursor to the bound ligand ($L^1$) in the final product; (b) a nucleophilic base; and (c) L or a precursor thereto, in (d) the presence of hydrogen gas, under conditions effective to provide the dihydrogen complex (VII):

(VII)

in a reaction mixture. Upon completion of the reaction and subsequent cooling, an alkyne of formula (VIII):

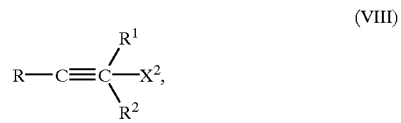

(VIII)

wherein R, $R^1$, $R^2$ and $X^2$ are as defined previously, is gradually added to the dihydrogen complex. An additional base may be added to neutralize the acid generated during formation of the dihydrogen complex (VII) and/or the nucleophilic base selected is one that is effective in this regard as well.

In another aspect of the invention, a method is provided for synthesizing a ligand precursor $L^1$-$CCl_3$ where $L^1$ is a heteroatom-stabilized carbene ligand as defined above, by contacting an ionized, unsaturated analog of $L^1$ with a non-nucleophilic base in the presence of chloroform. In a preferred embodiment, the ligand precursor has the structure of formula (XI):

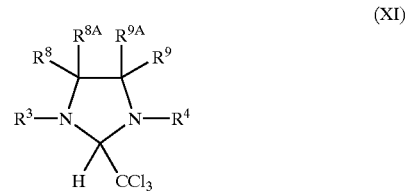

(XI)

in which $R^3$, $R^4$, $R^8$, $R^{8A}$, $R^9$, and $R^{9A}$ are substituents independently selected from the group consisting of hydrogen, hydrocarbyl, substituted hydrocarbyl, heteroatom-containing hydrocarbyl, substituted heteroatom-containing hydrocarbyl, and -$(Z)_n$-Fn where n is zero or 1, Z is hydrocarbylene, substituted hydrocarbylene and/or heteroatom-containing hydrocarbylene, and Fn is a functional group such as phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, boryl, halogen, stannyl, or germyl, any of which, if the substituent permits, may be further substituted with additional hydrocarbyl and/or -(Z)$_n$-Fn moieties, and further wherein any two or more of $R^3$, $R^4$, $R^8$, $R^{8A}$, $R^9$, and $R^{9A}$ are optionally linked to form a cyclic group.

In this embodiment, the synthetic method involves contacting a compound having the structure of formula (XII):

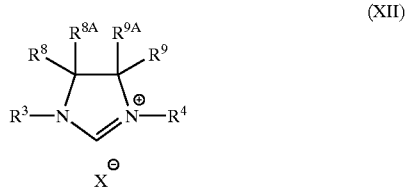

(XII)

with chloroform and a non-nucleophilic base effective to deprotonate the chloroform, wherein, in formula (XII), $X^-$ is an anionic counterion such as a halide ion. Examples of non-nucleophilic bases include inorganic hydroxides, metal hydrides, and organolithium reagents.

In other aspects of the invention, the ligand precursor (XI) is directly employed in any of a variety of ligand substitution reactions. For example, precursor (XI) may replace a phosphine ligand in a bisphosphine complex such as $(X^1)(X^2)(PR^5R^6R^7)_2M=CRR^{14}$ wherein M, $X^1$, $X^2$, and R are defined previously, $R^5$, $R^6$ and $R^7$ are each independently $C_5$–$C_{20}$ aryl or $C_1$–$C_{10}$ alkyl, including cycloalkyl, and $R^{14}$ is independently selected from the group consisting of hydrogen, hydrocarbyl, substituted hydrocarbyl, heteroatom-containing hydrocarbyl, substituted heteroatom-containing hydrocarbyl, and -(Z)$_n$-Fn where n, Z and Fn are defined earlier. In such a reaction, the bisphosphine complex is contacted with ligand precursor (XI) under conditions effective to provide the transition metal carbene complex (XIII):

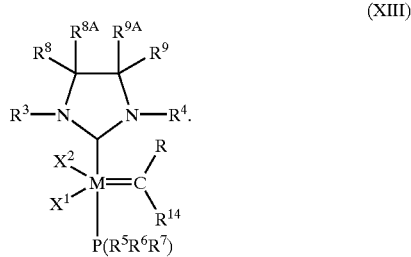

(XIII)

The invention also pertains to other such reactions wherein the trichloromethyl-substituted ligand precursor (XI) is used in an initial ligand substitution reaction, which is thereafter followed by one or more additional synthetic steps, often without need for isolation and purification of intermediates.

DETAILED DESCRIPTION OF THE INVENTION

I. Definitions and Nomenclature:

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a substituent" encompasses not only a single substituent but also two or more substituents that may be the same or different.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear, branched or cyclic saturated hydrocarbon group typically although not necessarily containing 1 to about 20 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched or cyclic alkyl group, where "alkyl" is as defined above.

The term "alkenyl" as used herein refers to a linear, branched or cyclic hydrocarbon group of 2 to 20 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched or cyclic alkenyl group, where "alkenyl" is as defined above.

The term "alkynyl" as used herein refers to a linear or branched hydrocarbon group of 2 to 20 carbon atoms containing at least one triple bond, such as ethynyl, n-propynyl, and the like. Preferred alkynyl groups herein contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety), generally containing in the range of 5 to 24 carbon atoms. Preferred aryl groups contain one aromatic ring or 2 to 4 fused or linked aromatic rings, e.g., phenyl, naphthyl, biphenyl, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the terms "aromatic," "aryl," and "arylene" include heteroaromatic, substituted aromatic, and substituted heteroaromatic species.

The term "aryloxy" as used herein refers to an aryl group bound through a single, terminal ether linkage. An "aryloxy" group may be represented as —O-aryl where aryl is as defined above.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The term "alicyclic" refers to an aliphatic cyclic moiety, which may or may not be bicyclic or polycyclic.

The term "amino" is used herein to refer to the group —NZ$^1$Z$^2$, where each of Z$^1$ and Z$^2$ is independently selected from the group consisting of hydrogen and optionally substituted alkyl, alkenyl, alkynyl, aryl, aralkyl, alkaryl and heterocyclic.

The terms "halo," halide" and halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

"Hydrocarbyl" refers to univalent hydrocarbyl radicals containing 1 to about 30 carbon atoms, preferably 1 to about 20 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, and the term "hydrocarbylene" intends a divalent hydrocarbyl moiety containing 1 to about 30 carbon atoms, preferably 1 to about 20 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl."

"substituted" as in "substituted hydrocarbyl," "substituted alkyl," "substituted aryl," and the like, as alluded to in some of the aforementioned definitions, is meant that in the hydrocarbyl, alkyl, aryl, or other moiety at least one hydrogen atom bound to a carbon (or other) atom is replaced with one or more non-hydrogen substituents. Examples of such substituents include, without limitation: functional groups such as halogen, phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, or boryl, or a metal-containing or metalloid-containing group (wherein the metal may be, for example, Sn or Ge); and the hydrocarbyl moieties $C_1$–$C_{20}$ alkyl, $C_2$–$C_{20}$ alkenyl, $C_2$–$C_{20}$ alkynyl, $C_5$–$C_{20}$ aryl, $C_5$–$C_{30}$ aralkyl, and $C_5$–$C_{30}$ alkaryl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

II. General Description of the Ligands and Catalysts Synthesized:

The methods of the present invention may be used to synthesize Group 8 transition metal carbene complexes that include a metal center in a +2 oxidation state, have an electron count of 16, and are penta-coordinated. More specifically, the methods of the present invention are useful in synthesizing compounds having the structure of formula (V):

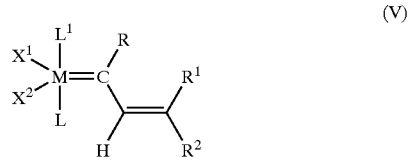

(V)

as well as compounds that serve as precursors to $L^1$ in the synthesis of complex (V). The various substituents are as follows:

M, which serves as the transition metal center in the +2 oxidation state, is a Group 8 transition metal, particularly ruthenium or osmium. In a preferred embodiment, M is ruthenium.

$X^1$ and $X^2$ may be the same or different, and are anionic ligands or polymers, and may be linked together to form a cyclic group, typically although not necessarily a five- to eight-membered ring. In preferred embodiments, $X^1$ and $X^2$ are each independently hydrogen, halide, or one of the following groups: $C_1$–$C_{20}$ alkyl, $C_5$–$C_{20}$ aryl, $C_1$–$C_{20}$ alkoxy, $C_5$–$C_{20}$ aryloxy, $C_3$–$C_{20}$ alkyldiketonate, $C_5$–$C_{20}$ aryldiketonate, $C_2$–$C_{20}$ alkoxycarbonyl, $C_5$–$C_{20}$ aryloxycarbonyl, $C_2$–$C_{20}$ acyl, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl. Optionally, $X^1$ and $X^2$ may be substituted with one or more moieties selected from the group consisting of $C_1$–$C_{10}$ alkyl, $C_1$–$C_{10}$ alkoxy, aryl, and halide, which may, in turn, with the exception of halide, be further substituted with one or more groups selected from halide, $C_1$–$C_6$ alkyl, $C_1$–$C_6$ alkoxy, and phenyl. In more preferred embodiments, $X^1$ and $X^2$ are halide, benzoate, $C_2$–$C_6$ acyl, $C_2$–$C_6$ alkoxycarbonyl, $C_1$–$C_6$ alkyl, phenoxy, $C_1$–$C_6$ alkoxy, $C_1$–$C_6$ alkylsulfanyl, $C_5$–$C_{20}$ aryl, or $C_1$–$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, $X^1$ and $X^2$ are each chloride. The complex may also be attached to a solid support, such as to a polymeric substrate, and this attachment may be effected by means of $X^1$ and/or $X^2$, in which case $X^1$ and/or $X^2$ is a polymer.

R, $R^1$ and $R^2$ are selected from the group consisting of hydrogen, hydrocarbyl (e.g., alkyl, alkenyl, alkynyl, aryl, aralkyl, alkaryl, etc.), substituted hydrocarbyl (e.g., substituted alkyl, alkenyl, alkynyl, aryl, aralkyl, alkaryl, etc.), heteroatom-containing hydrocarbyl (e.g., heteroatom-containing alkyl, alkenyl, alkynyl, aryl, aralkyl, alkaryl, etc.), and substituted heteroatom-containing hydrocarbyl (e.g., substituted heteroatom-containing alkyl, alkenyl, alkynyl, aryl, aralkyl, alkaryl, etc.), and -$(Z)_n$-Fn where n, Z and Fn are defined previously. $R^1$ and $R^2$ may also be linked to form a cyclic group, which may be aliphatic or aromatic, and may contain substituents and/or heteroatoms. Generally, such a cyclic group will contain 4 to 12, preferably 5 to 8, ring atoms.

In preferred catalysts, R is hydrogen and $R^1$ and $R^2$ are selected from the group consisting of hydrogen, $C_1$–$C_{20}$ alkyl, $C_5$–$C_{20}$ aryl, and -$(Z)_n$-Fn where Z is alkylene or substituted alkylene, and Fn is phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, boryl, halogen, stannyl, or germyl. More preferably, $R^1$ and $R^2$ are selected from the group consisting of hydrogen, $C_1$–$C_6$ alkyl, and $C_5$–$C_{20}$ aryl.

L is any neutral electron donor ligand, and may or may not be linked to $R^2$ or other substituents within the complex. Examples of suitable L moieties include, without limitation, phosphine, sulfonated phosphine, phosphite, phosphinite, phosphonite, arsine, stibine, ether (including cyclic ethers), amine, amide, imine, sulfoxide, carboxyl, nitrosyl, pyridine, substituted pyridine (e.g., halogenated pyridine), imidazole, substituted imidazole (e.g., halogenated imidazole), pyrazine (e.g., substituted pyrazine), and thioether. In more preferred embodiments, L is a phosphine of the formula $PR^5R^6R^7$, where $R^5$, $R^6$, and $R^7$ are each independently $C_5$–$C_2$ aryl or $C_1C_{10}$ alkyl, particularly phenyl, primary alkyl, secondary alkyl or cycloalkyl. In the most preferred embodiments, L is selected from the group consisting of —P(cyclohexyl)$_3$, —P(cyclopentyl)$_3$, —P(isopropyl)$_3$, —P(phenyl)$_3$, —P(phenyl)$_2(R^7)$ and —P(phenyl)$(R^7)_2$, in which $R^7$ is alkyl, typically lower alkyl. Also preferred are weaker ligands such as the nitrogen-containing heterocycles, which enhance catalytic activity presumably because of the requirement that the L ligand dissociate for initiation to occur. Examples of complexes wherein L and $R^2$ are linked include the following:

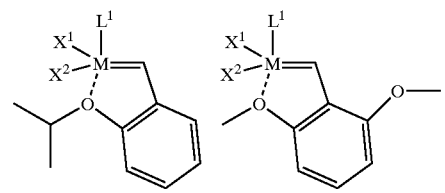

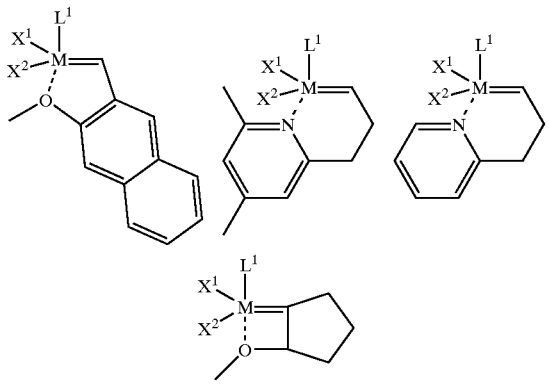

$L^1$ is a neutral electron donor ligand having the structure of formula (VI):

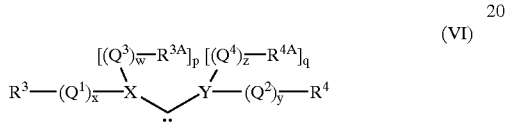

wherein X, Y, p, q, $Q^1$, $Q^2$, $Q^3$, $Q^4$, $R^3$, $R^{3A}$, $R^4$, $R^{4A}$, w, x, y and z are as follows:

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y and z are independently zero or 1, meaning that each linker is optional. Preferably, w, x, y and z are all zero.

$R^3$, $R^{3A}$, $R^4$, and $R^{4A}$ are independently selected from the group consisting of hydrogen, hydrocarbyl, substituted hydrocarbyl, heteroatom-containing hydrocarbyl, and substituted heteroatom-containing hydrocarbyl, wherein $R^{3A}$ and $R^{4A}$ may be linked to form a cyclic group.

It should be emphasized that any two or more (typically two, three or four) of $X^1$, $X^2$, L, $R^1$, $R^2$, $R^3$, $R^{3A}$, $R^4$, and $R^{4A}$ can be taken together to form a chelating multidentate ligand, as disclosed, for example, in U.S. Pat. No. 5,312,940 to Grubbs et al. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$—, —As(Ph)$_2$CH$_2$CH$_2$As (Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$— and —OC(CH$_3$)$_2$(CH$_3$)$_2$CO—. Preferred bidentate ligands are —P(Ph)$_2$ CH$_2$CH$_2$P(Ph)$_2$— and —P(CH$_3$)$_2$(CH$_2$)$_2$P (CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, L, $R^1$, $R^2$, $R^3$, $R^{3A}$, $R^4$, and $R^{4A}$ (e.g., X, L, and any one of $R^3$, $R^{3A}$, $R^4$, and $R^{4A}$) are taken together to be cyclopentadienyl, indenyl or fluorenyl, each optionally substituted with $C_2$–$C_{20}$ alkenyl, $C_2$–$C_{20}$ alkynyl, $C_1$–$C_{20}$ alkyl, $C_5$–$C_{20}$ aryl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkoxycarbonyl, $C_1$–$C_{20}$ alkylthio, $C_1$–$C_{20}$ alkylsulfonyl, or $C_1$–$C_{20}$ alkylsulfinyl, each of which may be further substituted with $C_1$–$C_6$ alkyl, halogen, $C_1$–$C_6$ alkoxy or with a phenyl group optionally substituted with halogen, $C_1$–$C_6$ alkyl or $C_1$–$C_6$ alkoxy. More preferably, in compounds of this type, X, L, and any one of $R^3$, $R^{3A}$, $R^4$, and $R^{4A}$ are taken together to be cyclopentadienyl or indenyl, each optionally substituted with vinyl, $C_1$–$C_{10}$ alkyl, $C_5$–$C_{20}$ aryl, $C_1$–$C_{10}$ carboxylate, $C_2$–$C_{10}$ alkoxycarbonyl, $C_1$–$C_{10}$ alkoxy, $C_5$–$C_{20}$ aryloxy, each optionally substituted with $C_1$–$C_6$ alkyl, halogen, $C_1$–$C_6$ alkoxy or with a phenyl group optionally substituted with halogen, $C_1$–$C_6$ alkyl or $C_1$–$C_6$ alkoxy. Most preferably, X, L, and any one of $R^3$, $R^{3A}$, $R^4$, and $R^{4A}$ may be taken together to be cyclopentadienyl, optionally substituted with vinyl, hydrogen, Me or Ph. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

In a preferred embodiment, w, x, y and z are zero, X and Y are N, and $R^{3A}$ and $R^{4A}$ are linked to form —Q—, such that $L^1$ has the structure of formula (IX):

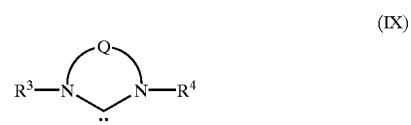

wherein Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group, which may be similarly substituted to provide a fused polycyclic structure of two to five cyclic groups. Q is often, although again not necessarily, a two-atom linkage or a three-atom linkage, e.g., —CH$_2$—CH$_2$—, —CH(Ph)—CH(Ph)— where Ph is phenyl; =CR—N=, giving rise to an unsubstituted (when R=H) or substituted (R=other than H) triazolyl group; and —CH$_2$—SiR$_2$—CH$_2$— (where R is H, alkyl, alkoxy, etc.).

In a more preferred embodiment, Q is a two-atom linkage having the structure —CR$^8$R$^{8A}$—CR$^9$R$^{9A}$— or —CR$^8$=CR$^9$—, more preferably —CR$^8$R$^{8A}$—CR$^9$R$^{9A}$—, in which case the complex has the structure of formula (XIV):

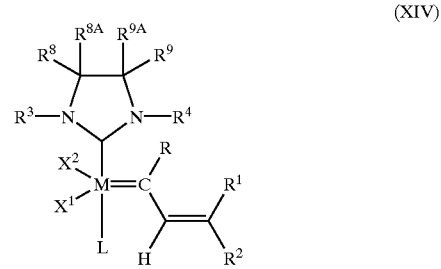

wherein $R^8$, $R^{8A}$, $R^9$, and $R^{9A}$ are independently selected from the group consisting of hydrogen, hydrocarbyl, substituted hydrocarbyl, heteroatom-containing hydrocarbyl, substituted heteroatom-containing hydrocarbyl, and may comprise a functional group Fn as defined previously. Preferred $R^8$, $R^{8A}$, $R^9$, and $R^{9A}$ moieties include, without limitation, $C_1$–$C_{20}$ alkyl, $C_2$–$C_{20}$ alkenyl, $C_2$–$C_{20}$ alkynyl, $C_5$–$C_{20}$ aryl, carboxyl, $C_1$–$C_{20}$ alkoxy, $C_2$–$C_{20}$ alkenyloxy, $C_2$–$C_{20}$ alkynyloxy, $C_5$–$C_{20}$ aryloxy, $C_2$–$C_{20}$ alkoxycarbonyl, $C_2$–$C_{20}$ alkoxycarbonyl, $C_1$–$C_{20}$ alkylthio, $C_5$–$C_{20}$ arylthio, $C_1$–$C_{20}$ alkylsulfonyl, and $C_1$–$C_{20}$ alkylsulfinyl, optionally substituted with one or more moieties selected from the group consisting of $C_1$–$C_{10}$ alkyl, $C_1$–$C_{10}$ alkoxy, $C_5$–$C_{20}$ aryl, hydroxyl, sulfhydryl, —(CO)—H, and halide.

Additionally, any two of $R^8$, $R^{8A}$, $R^9$, and $R^{9A}$ may be linked together to form a substituted or unsubstituted, saturated or unsaturated ring structure, e.g., a $C_4$–$C_{12}$ alicyclic group or a $C_5$ or $C_6$ aryl group, which may itself be substituted, e.g., with linked or fused alicyclic or aromatic groups, or with other substituents.

Examples of N-heterocyclic carbene ligands incorporated into complex (X) thus include, but are not limited to, the following:

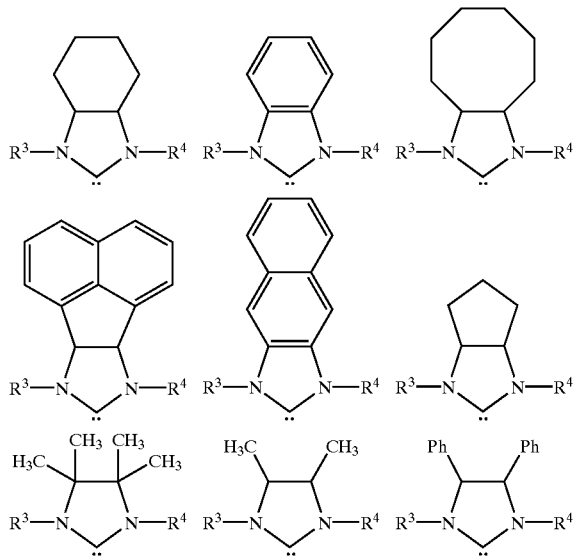

$R^3$ and $R^4$ are preferably aromatic, substituted aromatic, heteroaromatic, substituted heteroaromatic, alicyclic, or substituted alicyclic, composed of from one to about five cyclic groups. When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and have the structure (X):

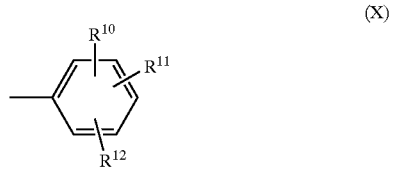

in which $R^{10}$, $R^{11}$, and $R^{12}$ are each independently hydrogen, $C_1$–$C_{20}$ alkyl, substituted $C_1$–$C_{20}$ alkyl, $C_1$–$C_{20}$ heteroalkyl, substituted $C_1$–$C_{20}$ heteroalkyl, $C_5$–$C_{20}$ aryl, substituted $C_5$–$C_{20}$ aryl, $C_5$–$C_{20}$ heteroaryl, $C_5$–$C_{30}$ aralkyl, $C_5$–$C_{30}$ alkaryl, or halogen. In especially preferred embodiments, $R^{10}$, $R^{11}$, and $R^{12}$ are each independently selected from the group consisting of hydrogen, methyl, ethyl, propyl, isopropyl, hydroxyl, halogen, phenyl, and lower alkyl-substituted phenyl. In the most preferred embodiments, $R^{10}$, $R^{11}$, and $R^{12}$ are the same and are each methyl.

Other catalysts may also be synthesized using the present methods, as will be discussed in detail infra. Such catalysts include analogs of alkylidene (V) wherein the M=CR—CH=$CR^1R^2$ moiety is replaced with M=$CRR^{14}$ wherein $R^{14}$ does not necessarily comprise a vinyl group, e.g., it may be alkyl or aryl, and in a preferred embodiment is phenyl. Other complexes that may be synthesized using the methods of the invention are vinylidene analogs of (V) wherein the M=CR—CH=$CR^1R^2$ moiety is replaced with M=C=CHR. Both of the latter analogs are readily prepared using a "chloroform adduct" of a carbene ligand, i.e., a trichloromethyl-substituted precursor to a carbene ligand.

III. One-Pot Synthesis of Transition Metal Alkylidenes:

One embodiment of the invention pertains to a method for synthesizing transition metal alkylidene complexes having the structure of formula (V):

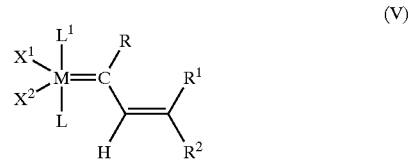

in which the various substituents are defined earlier herein. The synthesis is a two-step reaction involving formation of a transition metal dihydrogen complex substituted with the desired carbene ligand, followed by reaction with an alkyne to yield the metal alkylidene functionality.

A. Formation of the Dihydrogen Complex Intermediate:

In the initial step of the synthesis, a metal complex $ML^3(X^1)_2$, where M and $X^1$ are as defined above and $L^3$ is a bidentate organic ligand, is contacted with: (a) a salt or adduct of $L^1$, which serves as a precursor to the bound ligand ($L^1$) in the final product; (b) a nucleophilic base; and (c) L or a precursor thereto, in (d) the presence of hydrogen gas, under conditions effective to provide the dihydrogen complex (VII):

in a reaction mixture. An additional base may be added to neutralize the acid generated during formation of (VII) and/or the nucleophilic base selected is one that is effective in this regard as well.

The nucleophilic base is generally a nitrogenous base with some steric bulk, as some degree of steric encumbrance typically increases the yield of the dihydrogen complex and minimizes generation of other metal hydride species. Preferred nucleophilic bases contain secondary or tertiary alkyl moieties, cycloalkyl moieties, aryl groups, tri(alkyl)silyl groups, or the like, and particularly preferred nucleophilic bases have the structure $M^1N(SiR^{15}_3)_2$ wherein $M^1$ is an alkali metal, preferably potassium, and $R^{15}$ is hydrocarbyl, typically lower hydrocarbyl, and thus includes the lower alkyl groups methyl, ethyl, n-propyl, cyclohexyl. Such bases are more effective in the present method when a nonpolar organic solvent such as benzene, toluene, hexane, or the like is employed for the reaction. In addition, with nucleophilic bases of the formula $M^1N(SiR^x_3)_2$, there is generally no need for an additional base to remove the acid generated during formation of the dihydrogen complex, insofar as the $HN(SiR^x_3)_2$ generated from the deprotonation of the salt or ligand of $L^1$ (e.g., $IMesH_2Cl$), is typically sufficient to remove the acid (e.g., HCl) produced.

In a preferred embodiment, the salt or adduct of $L^1$ is a halide salt, e.g., a chloride salt, or a trichloromethyl-substituted carbene precursor as described in part (IV) of this section, infra. The ligand $L^3$ may be virtually any bidentate ligand that can detach in a ligand substitution reaction with the salt or adduct of $L^1$. Examples of ligands suitable as $L^3$ include $C_5$–$C_8$ cyclic dienes, optionally substituted and/or heteroatom containing. A particularly preferred $L^3$ is 1,5-cyclooctadiene.

Elevated temperatures are generally necessary, on the order of 55° C. to 90° C., although it will be appreciated that an optimum temperature for any particular reaction will depend on the selected starting materials. Hydrogen pressure in the reaction chamber will generally be maintained at about 20 psi to 30 psi, although the hydrogen pressure is not critical. The progress of the reaction may be monitored via NMR or using any other suitable means.

After cooling, the dihydrogen complex (VII) may be used in the remaining step of the synthesis without isolation and purification, since (VII) is routinely produced in high yield without a significant fraction of other metal hydrides. However, if desired, the dihydrogen complex can be isolated and purified at this point using conventional means, e.g., by column chromatography on silica gel.

B. Formation of the Dihydrogen Complex:

The second step of the reaction involves formation of the alkylidene at the transition metal center. Following preparation of (VII), cooling, and optional isolation and purification of the dihydrogen complex as described in (A), above, an alkyne of formula (VIII) is

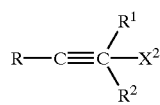

(VIII)

slowly added to the dihydrogen complex (which may be in the reaction mixture following its preparation in (A), or, if the complex has been isolated and purified, may be in solution in a suitable solvent). This reaction is generally, although not necessarily, carried out at a temperature in the range of about 5° C. to about 30° C. In formula (VIII), R, $R^1$, $R^2$ and $X^2$ are as defined previously.

Suitable alkynes for carrying out this reaction are described in U.S. Patent Publication No. 2002/0022733 A1 to Grubbs et al., and include, by way of example, compounds of formula (VIII) wherein R is hydrogen, $C_1$–$C_{20}$ alkyl, or $C_5$–$C_{20}$ aryl, $X^1$ is halide, and $R^1$ and $R^2$ are each $C_1$–$C_{20}$ alkyl, $C_5$–$C_{20}$ aryl, $C_1$–$C_{20}$ alkoxy, $C_5$–$C_{20}$ aryloxy, $C_1$–$C_{20}$ alkylsulfanyl, $C_5$–$C_{20}$ arylsulfanyl, $C_1$–$C_{20}$ alkylsulfinyl, $C_5$–$C_{20}$ arylsulfinyl, and may comprise functional groups Fn wherein Fn is defined previously. For any of the R, $R^1$ and $R^2$ moieties that permit further substitution, such moieties may further include substituents and/or heteroatoms that do not adversely affect the desired reaction. Particularly preferred alkynes are the propargylic halides H—C≡C—$C(CH_3)_2X^1$ wherein $X^1$ is halo, e.g., chloro or bromo.

The reaction between the alkyne and the dihydrogen complex (VII) proceeds quickly, even at a low temperatures. See Example 1, which describes synthesis of the alkylidene complex $(PCy_3)(IMesH_2)Cl_2Ru$=CH—CH=$C(CH_3)_2$ (2) via the dihydrogen complex $(PCy_3)(IMesH_2)Ru(H)(H_2)Cl$ (1). Following formation of (1), addition of propargyl chloride resulted in a nearly instantaneous reaction, yielding the desired alkylidene complex (2) in >95% yield. Reactions with other alkynes, particularly propargylic halides, also proceed rapidly and afford high yields of the transition metal alkylidene product.

IV. Preparation of "Chloroform Adducts" As Carbene Ligand Precursors:

In another embodiment, a method is provided for synthesizing a trichloromethyl-substituted ligand precursor having the structure $L^1$-$CCl_3$ wherein $L^1$ is defined in part (I) of this section. In a preferred embodiment, the ligand precursor $L^1$-$CCl_3$ has the structure (XI):

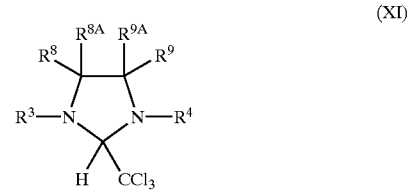

(XI)

in which $R^3$, $R^4$, $R^8$, $R^{8A}$, $R^9$, and $R^{9A}$ are as defined previously. This ligand precursor, or "chloroform adduct," is an optimal precursor to $L^1$ in the synthesis described in part (III), above. That is, compound (XI) serves as the salt or adduct of $L^1$ that is combined with the metal complex, the nucleophilic base, and L.

In this embodiment, an ionized, unsaturated analog of $L^1$ is reacted with chloroform and a base. In a preferred embodiment, compound (XI) is synthesized by contacting a compound having the structure of formula (XII):

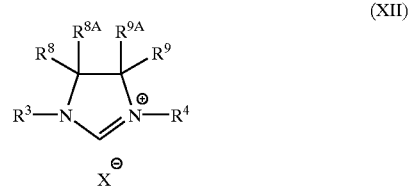

(XII)

(i.e., the ionized, unsaturated analog of $L^1$) with chloroform and a non-nucleophilic base effective to deprotonate the chloroform. Suitable bases include inorganic hydroxides, metal hydrides, and organolithium reagents such as t-butyllithium. Inorganic hydroxides include, by way of example, alkali metal hydroxides, alkaline earth metal hydroxides, e.g., sodium hydroxide, calcium hydroxide, potassium hydroxide, magnesium hydroxide, and the like. Preferred inorganic hydroxides are potassium hydroxide and sodium hydroxide, with potassium hydroxide particularly preferred. Metal hydrides include, but are not limited to, sodium hydride, lithium hydride, potassium hydride, rubidium hydride, cesium hydride, magnesium hydride, calcium hydride, strontium hydride, barium hydride, aluminum hydride, and combinations thereof. The metal hydride is preferably sodium hydride. Metal hydrides also include metal borohydrides, for example, lithium borohydride, potassium borohydride and sodium borohydride, although sodium hydride is particularly preferred. Organolithium reagents, as will be appreciated by those of ordinary skill in the art, include alkyllithium reagents such as methyl lithium, isopropyl lithium, n-butyllithium, s-butyllithium, t-butyllithium, and the like, as well as aryllithium lithium reagents, e.g., phenyl lithium and p-tolyl lithium.

The reaction will generally be carried out for a time period of about 0.5 to 4 hours at ambient temperature, although elevated temperatures may be beneficial or required under certain conditions. The chloroform may serve as the solvent, or an additional solvent may be employed. Any organic solvent can be used providing that there is no adverse impact on the desired reaction and that the reactants are sufficiently soluble therein. Suitable solvents include, solely by way of example, benzene, toluene, and tetrahydrofuran.

A series of experiments was carried out to evaluate the effect of various parameters on the aforementioned reaction, as described in Example 6. Chloroform was deprotonated with a variety of non-nucleophilic bases (including alkali metal hydroxides) and the resulting solution was added to the chloride 4,5-dihydroimidazolium salt (IMesH$_2$Cl) under varying temperatures and solvent conditions (Table 1).

TABLE 1

Variation of reaction parameters for the nucleophilic addition of trichloromethyl anion to 4,5-dihydroimidazolium salts.[a]

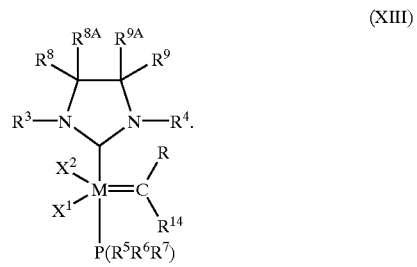

| Number of equiv. CHCl$_3$ | Solvent | Base | Temperature | Reaction Time | Yield |
|---|---|---|---|---|---|
| As solvent | CHCl$_3$ | NaOH | 25° C. | 2 hr. | 54% |
| 3.0 | THF | NaOH | reflux | 2 hr. | 59% |
| 3.0 | C$_6$H$_6$ | NaOH | 25° C. | 1.5 hr. | 67% |
| 3.0 | toluene | KOH | 25° C. | 2 hr. | 83% |

[a]The indicated base (in large excess) and chloroform are mixed (in the indicated solvent), followed by immediate addition of the imidazolium salt. After the indicated time, the reaction solution was filtered on a coarse frit to remove unreacted base and purified by passing the mother liquor through a silica gel plug (eluting with 9:1 hexanes:ethyl acetate.

After purification by recrystallization or column chromatography, the IMesH$_2$.CHCl$_3$ adduct could be isolated on the gram scale in 83–90% yields as pure crystalline material. This high-yielding adduct synthesis, using the easily handled base potassium hydroxide, represents the simplest procedure developed to date for the production of IMesH$_2$.CHCl$_3$ and analogs thereof. The synthesis can be readily carried out on the benchtop with non-dry, non-degassed solvents, and the use of potassium hydroxide prevents any large-scale flammability or reactivity problems. Exposure to potentially toxic chlorinated solvents (i.e. chloroform) in this procedure is also kept to a minimum.

As noted above, it is also possible to deprotonate chloroform with even stronger non-nucleophilic bases such as organolithium reagents (tert-butyllithium) and florene. These examples are noteworthy for their solubility in other non-polar solvents (such as hexanes or diethyl ether) which may be used. In a variety of cases these nonpolar solvents should be ideal to limit the solubility of the imidazolium salt, thereby minimizing the side reactions from dichlorocarbene formed in the reaction.

The aforementioned adduct synthesis was also found to be tolerant of a variety of substitution patterns on the 4,5-dihydro-imidazolium salt, including R$^3$ and/or R$^4$=substituted aryl and R$^8$ and/or R$^9$=aryl or alkyl (in structural formula (XI)). It is relevant to note that only 4,5-dihydroimidazolium salts form imidazolidenes—the aromatic imidazolium salts (i.e., the unsaturated analogs) never form these adducts under any conditions. Instead, the latter species undergo immediate deprotonation to directly form the free carbene.

An alternate way of obtaining the compound IMesH$_2$.CHCl$_3$ is by the reaction of an equimolar amount of a strong base such as sodium hydride with chloroform in the presence of the salt (II), as described in Example 4, part (a). By this route, higher yield and purity of the obtained product is achievable, eliminating any further purification. This reaction is relatively rapid and takes place at room temperature. The trichloromethyl anion is formed in low concentrations from the reaction of a strong base with chloroform itself. This can be pre-formed, standardized and stored for short a period at low temperature to prevent the formation of dichlorocarbene. Chloroform is also conveniently used as a single component recyclable system because bis-mesityl-imidazolium chloride and like compounds are soluble in it, thus acting as a solvent and reactant the entire reaction. If equimolar amounts of base and imidazolium (or other) salt are dissolved in chloroform, upon dissolution of the base, the trichloromethyl anion is formed and is readily uptaken by the imidazolium salt. In a few minutes, the base is depleted and the resulting product remains in solution while sodium chloride (the only solid byproduct) falls out of solution. This way, the byproducts are minimized, maximizing the yield and avoiding further purification.

Once the adduct (XI) is obtained in large quantity by the described method, it may be directly employed in a variety of ligand substitution reactions. In one embodiment, ligand precursor (XI) may replace a phosphine ligand in a bisphosphine complex such as (X$^1$)(X$^2$)(PR$^5$R$^6$R$^7$)$_2$M=CRR$^{14}$, below,

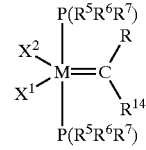

wherein M is Ru or Os, typically Ru, X$^1$ and X$^2$ are halides or other anionic ligands, R$^5$, R$^6$, and R$^7$ are each independently aryl or C$_1$–C$_{10}$ alkyl, including cycloalkyl, R is as defined previously, and R$^{14}$ is independently selected from the group consisting of hydrogen, hydrocarbyl, substituted hydrocarbyl, heteroatom-containing hydrocarbyl, substituted heteroatom-containing hydrocarbyl, and -(Z)$_n$-Fn where n, Z and Fn are defined earlier. In such a reaction, the bisphosphine complex is contacted with ligand precursor (XI) under conditions effective to provide the transition metal carbene complex (XIII):

(XIII)

As demonstrated in Table 2, the rate of this substitution reaction is strongly temperature-dependent. In general, the reaction does not proceed at any appreciable rate below 55° C. At 80° C., the substitution rate remains much slower than the rate of phosphine dissociation, suggesting that the rate-limiting step in these reactions is the decomposition of IMesH$_2$.CHCl$_3$ to the free carbene. Even at these high temperatures the ruthenium species appear to remain intact throughout the reaction, without the formation of hydrides or other byproducts.

TABLE 2

Ligand Substitution on ruthenium(II) metathesis catalysts.[a]

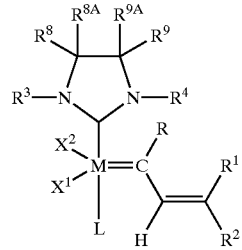

| Number of equiv. IMesH$_2$.CHCl$_3$ | Concentration of IMesH$_2$.CHCl$_3$ | Temperature | Reaction Rate ($k_{obs}$ × 10$^4$, s$^{-1}$)[b] |
|---|---|---|---|
| 1.0 | 0.04 M | 40° C. | NA |
| 1.0 | 0.04 M | 60° C. | 8.53 ± 0.33 |
| 2.0 | 0.08 M | 60° C. | 7.23 ± 0.12 |
| 5.0 | 0.20 M | 60° C. | 28.8 ± 2.6 |
| 5.0 | 0.20 M | 80° C. | 326 ± 14 |

[a]A solution of 3 in 0.25 mL C$_6$D$_6$ is prepared in a septum-capped NMR tube and equilibrated for 10 minutes at indicated temperature prior to injection of IMesH$_2$.CHCl$_3$ (in 0 25 mL C$_6$D$_6$)
[b]Determined by $^1$H NMR spectroscopy on a 300 MHz Oxford instrument running Varian VNMR software.

Another example of a ligand substitution reaction in which the ligand precursor (XI) has utility is in the synthesis of a transition metal alkylidene complex of formula (XIV):

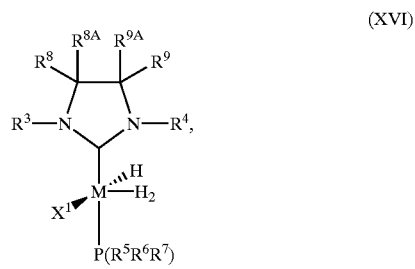

wherein M, X$^1$, X$^2$, L, R, R$^1$, R$^2$, R$^3$, R$^4$, R$^8$, R$^{8A}$, R$^9$, and R$^{9A}$ are as defined previously. The method circumvents the need for an excess of the salt or adduct of L$^1$ (e.g., IMesH$_2$Cl) used as a starting material in the direct substitution reaction described in part (III) of this section (see Example 4). In this embodiment, the route towards the transition metal alkylidene complex (XIV) is carried out as follows.

Initially, the ligand precursor (XI):

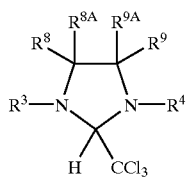

is contacted with a metal complex M(X$^1$)$_2$(L$^4$)$_2$, wherein X$^1$ is as defined previously and L$^4$ is an eta-6 coordinating ligand, e.g., an aromatic or substituted aromatic ligand such as p-cymene, under an inert atmosphere for a time period effective to allow the ligand substitution reaction to go to completion. The intermediate thereby provided, having the structure of formula (XV):

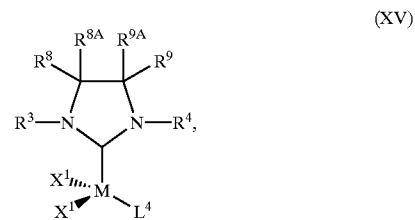

is then reacted with P(R$^5$R$^6$R$^7$) in the presence of hydrogen and a base, to give the dihydrogen complex (XVI):

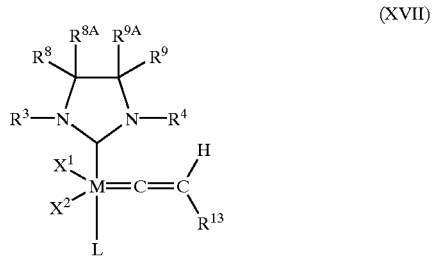

which is then treated with an alkyne of the formula (VIII):

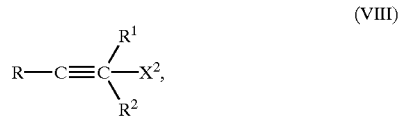

wherein R, R$^1$, R$^2$ and X$^2$ are as defined previously, as described in part (III) of this section.

The aforementioned method may be modified to provide a transition metal vinylidene product in lieu of the alkylidene (XIV). The vinylidene product will generally have the structure of formula (XVII):

(XVII)

[figure XVII]

wherein M, X$^1$, X$^2$, L, R$^3$, R$^4$, R$^8$, R$^{8A}$, R$^9$, and R$^{9A}$ are as defined previously, and R$^{13}$ is selected from the group consisting of hydrogen, hydrocarbyl, substituted hydrocarbyl, heteroatom-containing hydrocarbyl, substituted heteroatom-containing hydrocarbyl, and -(Z)$_n$-Fn where n is zero or 1, Z is a hydrocarbylene linkage, and Fn is a functional group.

This synthesis is a one-step method wherein intermediate (XV) is prepared as described above, and then directly treated with an alkyne of formula H—C≡C—R$^{13}$ and a tri-substituted phosphine (or other anionic ligand precursor).

It is to be understood that while the invention has been described in conjunction with the preferred specific embodiments thereof, that the foregoing description as well as the examples that follow are intended to illustrate and not limit the scope of the invention. It will be appreciated that various modifications may be made to the methodology of the invention, e.g., with respect to reaction conditions, starting materials, substituents, and the like, which will be recognized by those of ordinary skill in the art as within the spirit and scope of the invention.

All patents, patent applications, and publications mentioned herein are hereby incorporated by reference in their entireties.

EXPERIMENTAL

Anhydrous chloroform and toluene was obtained from Aldrich is degassed by bubbling dry nitrogen gas throughout. Potassium hydroxide was obtained from EM Science and powdered by mortar and pestle. Sodium hydride was obtained as a 95% dry solid from Aldrich. IMesH$_2$Cl was prepared according to a modified version of the procedure described in Scholl et al. (1999) *Org. Lett.* 1:953–956 and Jafarpour et al. (2000) *Organometallics* 19:2055–2057. Unless otherwise specified, all other reagents were purchased from commercial suppliers and used without further purification. All other solvents were purified by passage through a solvent column (containing activated A-2 alumina; see Pangborn et al. (1996) *Organometallics* 15:1518–1520.). Analytical thin-layer chromatography (TLC) was performed using silica gel 60 F254 precoated plates (0.25 mm thickness) with a fluorescent indicator. Flash column chromatography was performed using silica gel 60 (230–400 mesh) from EM Science. $^1$H, $^{13}$C, and $^{31}$P NMR spectra were obtained on a Varian 300 MHz Fourier Transform spectrometer (300 MHz $^1$H, 75.4 MHz $^{13}$C, 121.4 MHz $^{31}$P). All chemical shift values are given in parts-per million (δ) and are referenced with respect to residual solvent ($^1$H and $^{13}$C) or phosphoric acid ($^{31}$P). In Examples 1–3, all operations were performed under an inert atmosphere in a nitrogen-filled dry-box or by using standard Schlenk techniques.

Preparation of IMesH$_2$Cl: IMesH$_2$Cl, used as a starting material in Examples 1 through 3, was synthesized according to the following scheme:

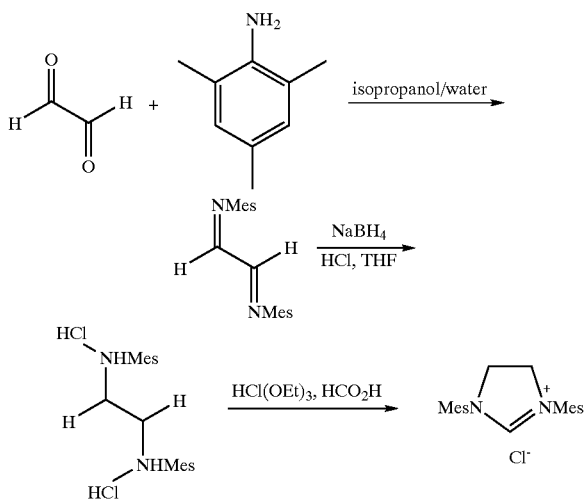

To a solution of glyoxal (9 mL, 79 mmol, 40% wt in H$_2$O) in isopropanol (100 mL) and H$_2$O (200 mL) was added mesitylamine (25 mL, 2.2 eq.) at 0° C. The reaction mixture was stirred while allowing to warm to room temperature. Immediately upon addition of amine, yellow precipitates were formed. After 24 hrs of stirring at ambient temperature, the precipitates were filtered and washed with H$_2$O (1×100 mL) and hexanes (3×100 mL). The yellow precipitates obtained were dried in vacuo to yield the diimine (20.6 g, 89%).

To a solution of diimine (8.0 g, 27.3 mmol) in THF (100 mL) was added NaBH4 (4.24 g, 112.1 mmol) at 0° C. Concentrated HCl (4.5 mL, 2 eq.) was added dropwise over 30 minutes. After the HCl addition, the reaction mixture was stirred at 0° C. for 20 min. Then, 3 M HCl (250 mL) was added carefully to the flask at 0° C. and the mixture was stirred for an additional 1 hr, allowing the temperature to rise to ambient temperature. The resulting white precipitates were filtered and washed with water (200 mL) and 5% acetone-ether (150 mL). The product (9.4 g, 93%) was obtained as a white solid and dried in vacuo. To a suspension of the HCl salt (8.5 g, 23 mmol) in HC(OEt)3 (35 mL, 162 mmol) was added 2 drops of HCO$_2$H (adding about 1 mol %). The reaction mixture was then heated at 120° C. for 5 hr under Ar. Then, the reaction mixture was cooled to an ambient temperature and hexane (200 mL) was added. The mixture was stirred for 1 hr and the white precipitates were filtered, washed with hexane (~200 mL) and dried in vacuo to yield the IMesH$_2$HCl salt (7.6 g, 96%).

EXAMPLE 1

Representative Procedure for Synthesis of Ruthenium Alkylidene Catalysts from Substituted Alkynes Synthesis of RuCl$_2$(=CH—CH=C(CH$_3$)$_2$)(IMesH$_2$) (PCy$_3$) (complex (2), Scheme 2):

SCHEME 2

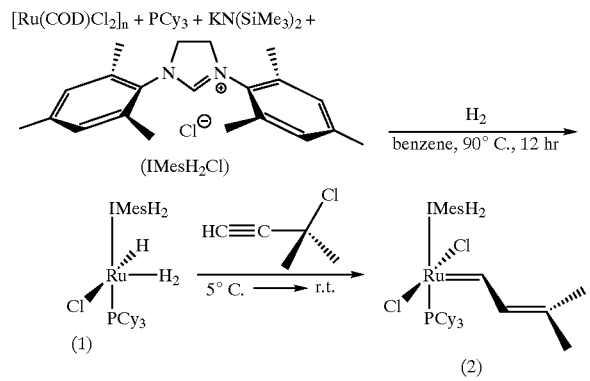

[Ru(COD)Cl$_2$]$_n$ (300 mg, 1 mmol), IMesH$_2$Cl (1.47 g, 4 mmol), tricyclohexylphosphine (300 mg, 1 mmol), and KN(SiMe$_3$)$_2$ (540 mg, 2.5 mmol) were weighed directly into a 600 mL Schlenk tube. The flask was evacuated and filled with dry argon (2×). Degassed benzene (300 mL) was added and the flask was pressurized to 30 psi with H$_2$. The suspension was vigorously stirred for 12 hours at 90° C., yielding a bright yellow solution and white precipitate (1). After cooling the reaction to 5° C., propargyl chloride (0.3 mL, 4 mmol) was slowly added via syringe and the reaction mixture was allowed to warm to room temperature. The resulting brown benzene solution was washed with degassed 1 M HCl (2×), degassed brine (2×), filtered through Celite and concentrated in vacuo to afford compound (2) as a brown solid in 90% yield (~95% purity). The brown solid displayed catalytic behavior identical with previously synthesized second-generation catalysts. Analytically pure (2) was obtained by column chromatography on silica gel (degassed 3:1 hexanes/Et$_2$O). $^1$H NMR (CD$_2$Cl$_2$): δ 18.49 (d, J=11.1 Hz, 1H), 7.26 (d, J=10.9 Hz, 1H), 6.97 (s, 2H), 6.77 (s, 2H), 3.92 (m, 4H), 2.58 (s, 6H), 2.37 (s, 6H), 2.29 (s, 3H), 2.23 (s, 3H), 0.88–1.584 (m, 33H), 1.06 (s, 3H), 1.08 (s, 3H). $^{31}$P NMR (CD$_2$Cl$_2$): δ 28.9. The reaction was repeated several times with one or more reaction conditions modified so as to optimize the yield of the product. It was found that the yield could be increased to greater than 95% by reducing the reaction temperature from 90° C. to 80° C.

Analogous ruthenium alkylidene complexes can be prepared using the aforementioned protocol and differently substituted phosphines, alkynes, etc., as indicated in the following two examples.

EXAMPLE 2

Scaled-Up Procedure for Synthesis of Complex (2) Ruthenium Alkylidene Catalysts from Substituted Alkynes After optimizing reaction conditions for the synthesis of Example 1, i.e., to afford high yields of complex (2), a large scale (~5 g) reaction was set up. A Schlenk flask containing a magnetic stir bar was charged with [RuCl$_2$(COD)]$_n$, IMesH$_2$Cl (4 equiv), and KN(SiMe$_3$)$_2$ (2.5 equiv) and placed under an atmosphere of argon. A benzene solution containing PCy$_3$ (1 equiv) was added via cannula and the flask was pressured with H$_2$ (30 psi). After stirring the reaction for 12 hours at 80° C., the flask was cooled to 5° C. and propargyl chloride was added via syringe. An immediate color change from yellow to brown occurred indicating the conversion of (1) to (2). The solution was washed with 1M HCl (1×) and brine (2×) then concentrated to give complex (2) as a fine tan powder in 90% yield.

EXAMPLE 3
Synthesis of RuCl$_2$(=CH—CH=C(CH$_3$)$_2$)(IMesH$_2$)(PPh$_3$) (Complex (4), Scheme 3):

SCHEME 3

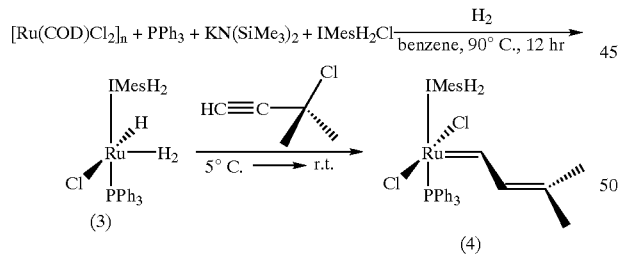

(3)   (4)

The procedure of Example 1 was employed using [Ru(COD)Cl$_2$]$_n$ (300 mg, 1 mmol), IMesH$_2$Cl (0.74 g, 2 mmol), triphenylphosphine (280 mg, 1 mmol), and KN(SiMe$_3$)$_2$ (380 mg, 1.9 mmol), giving 550 mg (68%) of complex (4). $^{31}$P NMR (CD$_2$Cl$_2$): δ 24.0. $^1$H NMR (CD$_2$Cl$_2$): δ 18.49 (d, J=11.1 Hz, 1H).

EXAMPLE 4

As may be deduced from Example 1, an excess of IMesH$_2$Cl is needed to optimize the yield of the product (decomposition of IMesH$_2$ was determined to be competitive with formation of the hydride intermediate RuCl(H)(H$_2$)(IMesH$_2$)(PCy$_3$)(1). To circumvent the need for excess IMesH$_2$Cl, synthesis of the intermediate (1) was carried out with a ruthenium complex that was pre-ligated with an imidazolylidene ligand, RuCl$_2$(IMesH$_2$)(p-cymene), as follows:

(a) Preparation of IMesH$_2$ chloroform adduct, IMesH$_2$—CCl$_3$ (2-trichloromethyl-1,3-mesityl-4,5-dihydroimidazol-2-ylidene) (compound (5), Scheme 4):

SCHEME 4

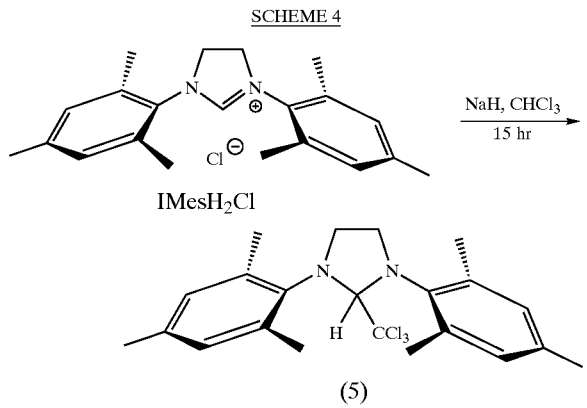

(5)

IMesH$_2$Cl (10 g, 29 mmol) was dissolved in dry, degassed chloroform (250 mL) in a flame dried 1000 mL round-bottomed flask equipped with stirbar. Sodium hydride (695 mg, 29 mmol) was then slowly added to the flask, and the resulting suspension was rapidly stirred at room temperature for 90 minutes. It was then vacuum filtered to remove precipitated sodium chloride, and concentrated in vacuo to a white solid. The product was further purified by recrystallization from boiling hexanes to give a white crystalline solid (11.7 g, 94% yield). $^1$H NMR (CD$_2$Cl$_2$): δ 6.877 (s, 2H), 6.854 (s, 2H), 5.595 (s, 1H), 3.92 (m, 2H), 3.31 (m, 2H), 2.496 (s, 6H), 2.461 (s, 6H), 2.26 (s, 6H). $^{13}$C NMR (CD$_2$Cl$_2$): δ 142.164 (s), 138.594 (s), 135.229 (s), 134.346 (s), 130.834 (s), 130.546 (s), 109.468 (s), 86.503(s), 52.318 (s), 21.780 (s), 21.005 (s), 20.268 (s).

Synthesis of RuCl$_2$(IMesH$_2$)(p-cymene) (Complex (6), Scheme 5):

SCHEME 5

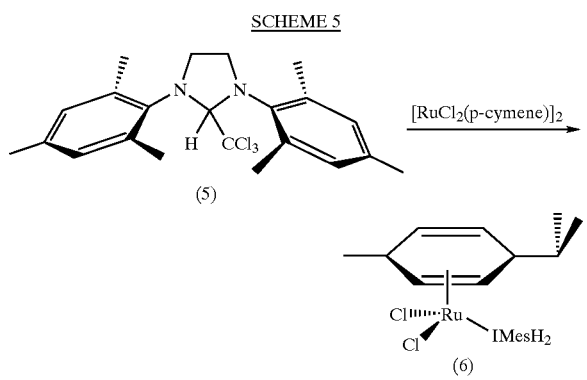

(6)

[(p-cymene)RuCl$_2$]$_2$ (80 mg, 0.13 mmol) and chloroform adduct (5) formed in (a) (140 mg, 0.3 mmol) were weighed into a round bottom flask equipped with a magnetic stir bar and reflux condenser. A hexanes:benzene mixture (10:1, 4 mL) was added and the reaction was placed under an argon atmosphere. After 4 hours of reflux, the reaction was cooled to room temperature and the tan precipitate was collected, washed with copious amounts of hexanes and dried in vacuo to afford the desired product (6) quantitatively. $^1$H NMR ($C_6D_6$): δ 6.523 (s, 4H), 5.254 (d, 2H), 4.882 (d, 2H), 3.948 (bs, 4H), 3.288 (m, 1H), 2.105 (s, 3H), 2.072 (s, 12H), 2.011 (s, 6H), 1.268 (d, 6H).

EXAMPLE 5

Synthesis of $(PCy_3)(IMesH_2)Cl_2Ru=C=C(CH_3)_3$ (complex (7), Scheme 6):

SCHEME 6

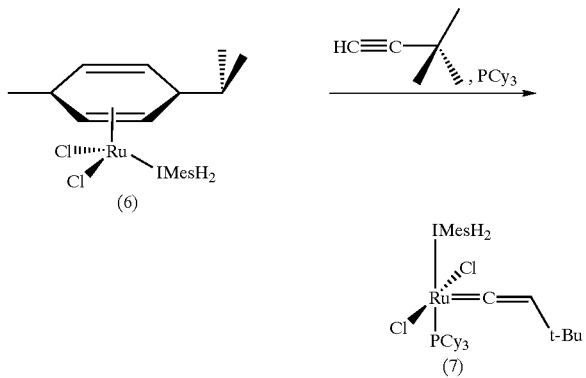

The p-cymene complex prepared in Example 4(b) can also be used directly, without isolation or purification, in the synthesis of metal vinylidene complexes. The following describes such a method, wherein $RuCl_2(IMesH_2)$(p-cymene) (6) is converted to the vinylidene complex $(PCy_3)(IMesH_2)Cl_2Ru=C=C(CH_3)_3$ (7), as illustrated in Scheme 5: $RuCl_2(IMesH_2)$(p-cymene), prepared in Example 4 (10 mg, 0.016 mmol), $PCy_3$ (5 mg, 0.016 mmol), and t-butyl acetylene (2 μL, 0.016 mmol) were dissolved in 0.6 mL $C_6D_6$ and transferred to a screw top NMR tube. The reaction was heated to 80° C. for 8 hours to afford (7).

EXAMPLE 6

Synthesis of Chloroform Adducts With Potassium Hydroxide

General Procedures. Potassium hydroxide was powdered with a mortar and pestle immediately prior to use. Anhydrous chloroform was used as obtained from Aldrich Chemical Company. Deuterated solvents were used as obtained from Cambridge Scientific. NMR spectra were recorded on Oxford Instruments 300 MHz NMR spectrometers running Varian VNMR software.

General procedure for NMR screening. Powdered potassium hydroxide (20 mg) was added to a screw-cap 10 dram vial equipped with stirbar. Deuterated benzene (0.7 mL) was added to the solid via syringe, forming a thick suspension. Chloroform (10 μL, 129 μmol, 3 eq.) was then added to the rapidly stirred suspension at room temperature. After 15 minutes, the imidazolium salt (either chloride or tetrafluoroborate counterion, 43 μmol, 1 eq.) was added to the suspension as a solid. After 30–45 minutes, the supernatant was decanted into a screw-cap NMR tube and the $^1$H NMR spectrum was recorded. In each case the ipso proton (N—C(H)($CCl_3$)—N) was cleanly observed in the range of 5.0–5.8 ppm.

Representative procedure for chloroform adduct formation (Table 1): Dry, degassed toluene (8.2 mL) was added to a flame dried 50 mL round-bottomed flask equipped with stirbar and reflux condenser. A large excess of potassium hydroxide (>10 mmol) was added to the flask, and the resulting suspension was rapidly stirred at room temperature. Chloroform (77 μL, 0.96 mmol) was added to this suspension via microsyringe. After 10 minutes, $IMesH_2Cl$ (100 mg, 0.29 mmol) was added, and the reaction mixture was then heated to 60° C. for 75 minutes. The mixture was allowed to cool to room temperature, vacuum filtered, and concentrated in vacuo to a yellowish-white solid. This crude product was then purified by filtration through a silica gel plug, eluting with 9:1 hexanes:ethyl acetate. The product was further purified by recrystallization from boiling hexanes to give a white solid (110 mg, 88% yield). The reaction was repeated with one or more different reaction parameters (e.g., base, solvent, temperature, time), with results indicated in Table 1.

EXAMPLE 7

Preparation of Ruthenium Alkylidene Catalysts

Preparation of ruthenium alkylidene catalysts coordinated with imidazolylidenes derived from the chloroform adducts synthesized in Example 6 (Table 2). To a solution of chloroform adduct (approximately 21 μmol) in deuterated benzene (0.7 mL) was added bis-(tricyclohexylphosphine) dichlororuthenium (II) benzylidene (9 mg, 11 μmol) as a solid. Periodic $^1$H NMR spectra were recorded at 10 degree intervals between room temperature and 80° C. Formation of new complexes was observed in the 18–22 ppm region of the $^1$H NMR spectra.

We claim:

1. A method for synthesizing a transition metal carbene complex having the structure of formula (V):

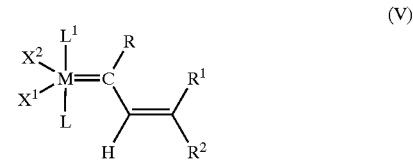

in which
M is a Group 8 transition metal,
$X^1$ and $X^2$ may be the same or different, and are anionic ligands or polymers;
R, $R^1$ and $R^2$ are independently selected from the group consisting of hydrogen, hydrocarbyl, substituted hydrocarbyl, heteroatom-containing hydrocarbyl, substituted heteroatom-containing hydrocarbyl, and -$(Z)_n$-Fn where n is zero or 1, Z is a hydrocarbylene, substituted hydrocarbylene and/or heteroatom-containing hydrocarbylene linkage, and Fn is a functional group;
L is any neutral electron donor ligand;
$L^1$ is a neutral electron donor ligand having the structure of formula (VI):

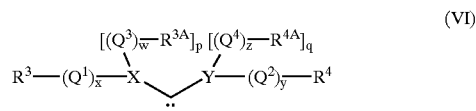

wherein
X and Y are heteroatoms selected from N, O, S, and P,
p is zero when X is O or S, and is 1 when X is N or P, q is zero when Y is O or S, and is 1 when Y is N or P,
$Q^1$, $Q^2$, $Q^3$, and $Q^4$ are selected from hydrocarbylene, substituted hydrocarbylene, heteroatom-containing hydrocarbylene, substituted heteroatom-containing hydrocarbylene, and —(CO)—;

w, x, y and z are independently zero or 1; and $R^3$, $R^{3A}$, $R^4$, and $R^{4A}$ are independently selected from the group consisting of hydrogen, hydrocarbyl, substituted hydrocarbyl, heteroatom-containing hydrocarbyl, and substituted heteroatom-containing hydrocarbyl, wherein any two or more of $X^1$, $X^2$, L, R, $R^1$, and $R^2$ can be taken together to form a chelating multidentate ligand, the method comprising:

(a) combining (i) a metal complex $ML^3(X^1)_2$, where M and $X^1$ are as defined above and $L^3$ is a bidentate organic ligand, with (ii) a salt or adduct of $L^1$, (iii) a nucleophilic base; and (c) L, in (d) the presence of hydrogen gas, under conditions effective to provide the dihydrogen complex (VII):

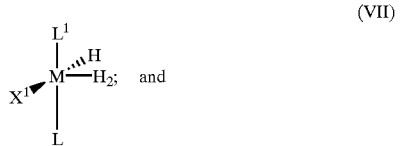

(VII)

(b) contacting the dihydrogen complex (VII) with an alkyne of the formula (VIII):

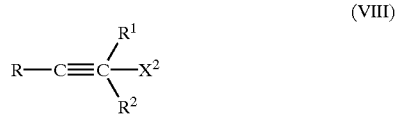

(VIII)

wherein R, $R^1$, $R^2$ and $X^2$ are as defined previously.

2. The method of claim 1, wherein M is Ru or Os.

3. The method of claim 2, wherein the salt or adduct of $L^1$ is selected from a halide salt and a trichloromethyl adduct.

4. The method of claim 2, wherein the nucleophilic base is a nitrogenous base containing at least one substituent selected from secondary alkyl, tertiary alkyl, cycloalkyl, aryl, and tri(alkyl)silyl groups.

5. The method of claim 4, wherein the nucleophilic base is of the formula $M^1N(SiR^{15}_3)_2$ in which $M^1$ is an alkali metal and $R^{15}$ is alkyl.

6. The method of claim 5, wherein the nucleophilic base is $KN[Si(CH_3)_3]_2$.

7. The method of claim 2, wherein step (a) is carried out in a substantially nonpolar solvent at a temperature in the range of approximately 55° C. to approximately 90° C.

8. The method of claim 2, wherein L is a neutral electron donor ligand selected from the group consisting of phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether.

9. The method of claim 8, wherein L is a phosphine of the formula $PR^5R^6R^7$, where $R^5$, $R^6$, and $R^7$ are each independently aryl or $C_1$–$C_{10}$ alkyl.

10. The method of claim 9, wherein L is selected from the group consisting of tricyclohexylphosphine, tricyclopentylphosphine, triisopropylphosphine, triphenylphosphine, diphenylmethylphosphine, and phenyldimethylphosphine.

11. The method of claim 2, wherein $L^3$ is 1,5-cyclooctadiene.

12. The method of claim 2, wherein w, x, y and z are zero, X and Y are N, and $R^{3A}$ and $R^{4A}$ are linked to form —Q—, such that $L^1$ has the structure of formula (IX):

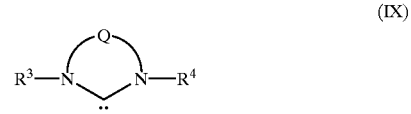

(IX)

wherein Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group.

13. The method of claim 12, wherein Q has the structure —$CR^8R^{8A}$—$CR^9R^{9A}$— or —$CR^8$=$CR^9$—, wherein $R^8$, $R^{8A}$, $R^9$, and $R^{9A}$ are substituents independently selected from the group consisting of hydrogen, hydrocarbyl, substituted hydrocarbyl, heteroatom-containing hydrocarbyl, substituted heteroatom-containing hydrocarbyl, and -$(Z)_n$-Fn where n is zero or 1, Z is alkylene or substituted alkylene, and Fn is phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, boryl, halogen, stannyl, or germyl, any of which, if the substituent permits, may be further substituted with additional hydrocarbyl and/or -$(Z)_n$-Fn moieties, and further wherein any two or more of $R^3$, $R^4$, $R^8$, $R^{8A}$, $R^9$, and $R^{9A}$ are optionally linked to form a cyclic group.

14. The method of claim 13, wherein Q has the structure —$CR^8R^{8A}$—$CR^9R^{9A}$—.

15. The method of claim 14, wherein:

$X^1$ and $X^2$ are independently selected from the group consisting of hydrogen, halide, $C_1$–$C_{20}$ alkyl, $C_5$–$C_{20}$ aryl, $C_1$–$C_{20}$ alkoxy, $C_5$–$C_{20}$ aryloxy, $C_3$–$C_{20}$ alkyldiketonate, $C_5$–$C_{20}$ aryldiketonate, $C_2$–$C_{20}$ alkoxycarbonyl, $C_1$–$C_{20}$ aryloxycarbonyl, $C_2$–$C_{20}$ acyl, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl, any of which, with the exception of hydrogen and halide, are optionally further substituted with one or more groups selected from halide, $C_1$–$C_6$ alkyl, $C_1$–$C_6$ alkoxy, and phenyl;

R is hydrogen and $R^1$ and $R^2$ are selected from the group consisting of hydrogen, $C_1$–$C_{20}$ alkyl, $C_5$–$C_{20}$ aryl, and -$(Z)_n$-Fn where Z is alkylene or substituted alkylene, and Fn is phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, boryl, halogen, stannyl, or germyl;

$R^3$ and $R^4$ are aromatic, substituted aromatic, heteroaromatic, substituted heteroaromatic, alicyclic, substituted alicyclic, heteroatom-containing alicyclic, or substituted heteroatom-containing alicyclic, composed of from one to about five rings; and $R^8$ and $R^9$ are hydrogen, and $R^{8A}$ and $R^{9A}$ are selected from hydrogen, lower alkyl and phenyl, or are linked to form a cyclic group.

16. The method of claim 15, wherein:

$X^1$ and $X^2$ are independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate;

$R^1$ and $R^2$ are selected from the group consisting of hydrogen, $C_1$–$C_6$ alkyl, and $C_5$–$C_{20}$ aryl; and $R^3$ and $R^4$ are the same and are either aromatic or $C_7$–$C_{12}$ alicyclic, if aromatic, each having the structure (X):

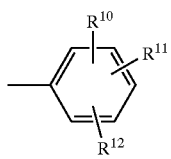

in which $R^{10}$, $R^{11}$, and $R^{12}$ are each independently hydrogen, $C_1$–$C_{20}$ alkyl, substituted $C_1$–$C_{20}$ alkyl, $C_1$–$C_{20}$ heteroalkyl, substituted $C_1$–$C_{20}$ heteroalkyl, $C_5$–$C_{20}$ aryl, substituted $C_5$–$C_{20}$ aryl, $C_5$–$C_{20}$ heteroaryl, $C_5$–$C_{30}$ aralkyl, $C_5$–$C_{30}$ alkaryl, or halogen.

17. The method of claim 16, wherein:

$X^1$ and $X^2$ are halide;

$R^1$ and $R^2$ are methyl;

$R^3$ and $R^4$ are mesityl;

L is selected from the group consisting of —P(cyclohexyl)$_3$ and —P(cyclopentyl)$_3$; and $R^{8A}$ and $R^{9A}$ are hydrogen.

18. A method for synthesizing a ligand precursor having the structure of formula (XI):

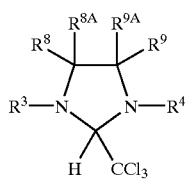

in which $R^3$, $R^4$, $R^8$, $R^{8A}$, $R^9$, and $R^{9A}$ are substituents independently selected from the group consisting of hydrogen, hydrocarbyl, substituted hydrocarbyl, heteroatom-containing hydrocarbyl, substituted heteroatom-containing hydrocarbyl, and -(Z)$_n$-Fn where n is zero or 1, Z is Z is hydrocarbylene, substituted hydrocarbylene and/or heteroatom-containing hydrocarbylene, and Fn is phosphonato, phosphoryl, phosphanyl, phosphino, sulfonato, $C_1$–$C_{20}$ alkylsulfanyl, $C_5$–$C_{20}$ arylsulfanyl, $C_1$–$C_{20}$ alkylsulfonyl, $C_5$–$C_{20}$ arylsulfonyl, $C_1$–$C_{20}$ alkylsulfinyl, $C_5$–$C_{20}$ arylsulfinyl, sulfonamido, amino, amido, imino, nitro, nitroso, hydroxyl, $C_1$–$C_{20}$ alkoxy, $C_5$–$C_{20}$ aryloxy, $C_2$–$C_{20}$ alkoxycarbonyl, $C_5$–$C_{20}$ aryloxycarbonyl, carboxyl, carboxylato, mercapto, formyl, $C_1$–$C_{20}$ thioester, cyano, cyanato, carbamoyl, epoxy, styrenyl, silyl, silyloxy, silanyl, siloxazanyl, boronato, boryl, halogen, stannyl, or germyl, any of which, if the substituent permits, may be further substituted with additional hydrocarbyl and/or -(Z)$_n$-Fn moieties, and further wherein any two or more of $R^3$, $R^4$, $R^8$, $R^{8A}$, $R^9$, and $R^{9A}$ are optionally linked to form a cyclic group, wherein the method comprises:
contacting a compound having the structure of formula (XII):

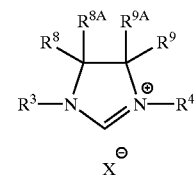

with chloroform and a non-nucleophilic base effective to deprotonate the chloroform, wherein, in formula (XII), $X^-$ is an anionic counterion.

19. The method of claim 18, wherein the non-nucleophilic base is an inorganic hydroxide, a metal hydride, or an organolithium reagent.

20. The method of claim 19, wherein the non-nucleophilic base is an alkali metal hydroxide.

21. The method of claim 19, wherein the non-nucleophilic base is sodium hydride.

22. The method of claim 18, wherein $X^-$ is a halide ion.

23. A method for synthesizing a transition metal carbene complex from the bisphosphine complex $(X^1)(X^2)(PR^5R^6R^7)_2M{=}CRR^{14}$ wherein M is Ru or Os, $X^1$ and $X^2$ are anionic ligands, $R^5$, $R^6$, and $R^7$ are each independently aryl or $C_1$–$C_{10}$ alkyl, and R and $R^{14}$ are independently selected from the group consisting of hydrogen, hydrocarbyl, substituted hydrocarbyl, heteroatom-containing hydrocarbyl, substituted heteroatom-containing hydrocarbyl, and -(Z)$_n$-Fn where n is zero or 1, Z is hydrocarbylene, substituted hydrocarbylene and/or heteroatom-containing hydrocarbylene, and Fn is a functional group, wherein the method comprises:

contacting the bisphosphine complex with a ligand precursor having the formula (XI):

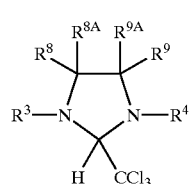

in which $R^3$, $R^4$, $R^8$, $R^{8A}$, $R^9$, and $R^{9A}$ are substituents independently selected from the group consisting of hydrogen, hydrocarbyl, substituted hydrocarbyl, heteroatom-containing hydrocarbyl, substituted heteroatom-containing hydrocarbyl, and -(Z)$_n$-Fn, thereby providing the transition metal carbene complex (XIII):

(XIII)

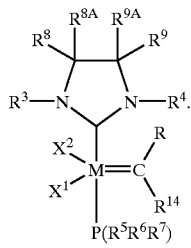

24. The method of claim 23, wherein:
M is Ru;
$X^1$ and $X^2$ are independently selected from the group consisting of hydrogen, halide, $C_1$–$C_{20}$ alkyl, $C_5$–$C_{20}$ aryl, $C_1$–$C_{20}$ alkoxy, $C_5$–$C_{20}$ aryloxy, $C_3$–$C_{20}$ alkyldiketonate, $C_5$–$C_{20}$ aryldiketonate, $C_2$–$C_{20}$ alkoxycarbonyl, $C_5$–$C_{20}$ aryloxycarbonyl, $C_2$–$C_{20}$ acyl, $C_1$–$C_{20}$ alkylsulfonato, $C_5$–$C_{20}$ arylsulfonato, $C_1$–$C_{20}$ alkylsulfanyl, $C_5$–$C_{20}$ arylsulfanyl, $C_1$–$C_{20}$ alkylsulfinyl, or $C_5$–$C_{20}$ arylsulfinyl, any of which, with the exception of hydrogen and halide are optionally further substituted with one or more groups selected from halide, $C_1$–$C_6$ alkyl, $C_1$–$C_6$ alkoxy, and phenyl;
R is hydrogen;
$R^{14}$ is selected from the group consisting of hydrogen, $C_1$–$C_{20}$ alkyl, $C_5$–$C_{20}$ aryl;
$R^3$ and $R^4$ are aromatic, substituted aromatic, heteroaromatic, substituted heteroaromatic, alicyclic, substituted alicyclic, heteroatom-containing alicyclic, or substituted heteroatom-containing alicyclic, composed of from one to about five rings; and
$R^8$ and $R^9$ are hydrogen, and $R^{8A}$ and $R^{9A}$ are selected from hydrogen, lower alkyl and phenyl, or are linked to form a cyclic group.

25. The method of claim 24, wherein the bisphosphine complex is (phenylmethylene-bis(tricyclohexylphosphine) ruthenium dichloride and the ligand precursor is 2-trichloromethyl-4,5-dihydroimidazolidine.

26. A method for synthesizing a transition metal alkylidene complex of formula (XIV):

(XIV)

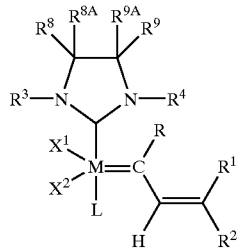

wherein M is Ru or Os, $X^1$ and $X^2$ are anionic ligands, L is $P(R^5R^6R^7)$, $R^5$, $R^6$, and $R^7$ are each independently aryl or $C_1$–$C_{10}$ alkyl, R, $R^1$ and $R^2$ are independently selected from the group consisting of hydrogen, hydrocarbyl, substituted hydrocarbyl, heteroatom-containing hydrocarbyl, substituted heteroatom-containing hydrocarbyl, and -$(Z)_n$-Fn where n is zero or 1, Z is a hydrocarbylene linkage, and Fn is a functional group, and $R^3$, $R^4$, $R^8$, $R^{8A}$, $R^9$, and $R^{9A}$ are substituents independently selected from the group consisting of hydrogen, hydrocarbyl, substituted hydrocarbyl, heteroatom-containing hydrocarbyl, substituted heteroatom-containing hydrocarbyl, and -$(Z)_n$-Fn, wherein the method comprises:
(a) contacting the ligand precursor (XI):

(XI)

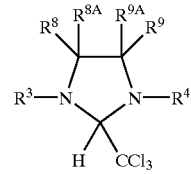

with $M(X^1)_2(L^4)_2$, wherein $L^4$ is an eta-6 coordinating ligand, to provide the intermediate (XV):

(XV)

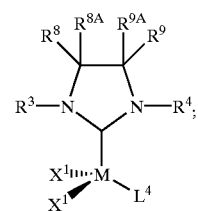

(b) contacting intermediate (XV) with $P(R^5R^6R^7)$ in the presence of hydrogen and a base, to give the dihydrogen complex (XVI):

(XVI)

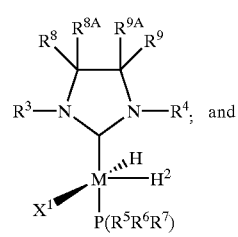

(d) thereafter treating the dihydrogen complex (XVI) with an alkyne of the formula (VIII):

(VIII)

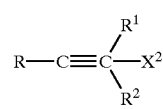

wherein R, $R^1$, $R^2$ and $X^2$ are as defined previously.

27. A method for synthesizing a transition metal vinylidene complex of formula (XVII):

(XVII)

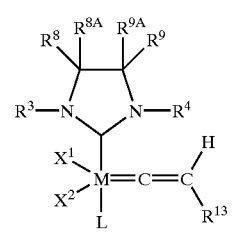

wherein M is Ru or Os, $X^1$ and $X^2$ are anionic ligands, $R^{13}$ is selected from the group consisting of hydrogen, hydrocarbyl, substituted hydrocarbyl, heteroatom-containing hydrocarbyl, substituted heteroatom-containing hydrocarbyl, and $-(Z)_n$-Fn where n is zero or 1, Z is a hydrocarbylene linkage, and Fn is a functional group, and $R^3$, $R^4$, $R^8$, $R^{8A}$, $R^9$, and $R^{9A}$ are substituents independently selected from the group consisting of hydrogen, hydrocarbyl, substituted hydrocarbyl, heteroatom-containing hydrocarbyl, substituted heteroatom-containing hydrocarbyl, and $-(Z)_n$-Fn, wherein the method comprises:

(a) contacting the ligand precursor (XI):

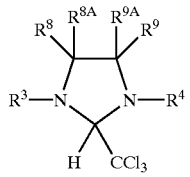

(XI)

with $MX^1X^2(L^4)_2$, wherein $L^4$ is an eta-6 coordinating ligand, to provide the intermediate (XV):

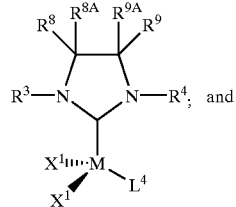

(XV)

thereafter treating intermediate (XIV) with an alkyne of the formula $H-C{\equiv}C-R^{13}$.

* * * * *

UNITED STATES PATENT AND TRADEMARK OFFICE
CERTIFICATE OF CORRECTION

PATENT NO. : 6,613,910 B2
DATED : September 2, 2003
INVENTOR(S) : Robert H. Grubbs et al.

It is certified that error appears in the above-identified patent and that said Letters Patent is hereby corrected as shown below:

Column 29,
Line 53, please delete "C." and insert -- C --

Column 30,
Line 45, please delete "$C_1$" and insert -- $C_5$ --

Column 33,
Line 15, please delete "$x^2$" and insert -- $X^2$ --

Column 36,
Line 12, in chemical structure (XV) please delete the last occurrence of "$X^1$" and insert -- $X^2$ --. The corrected structure will appear as follows:

(XV)
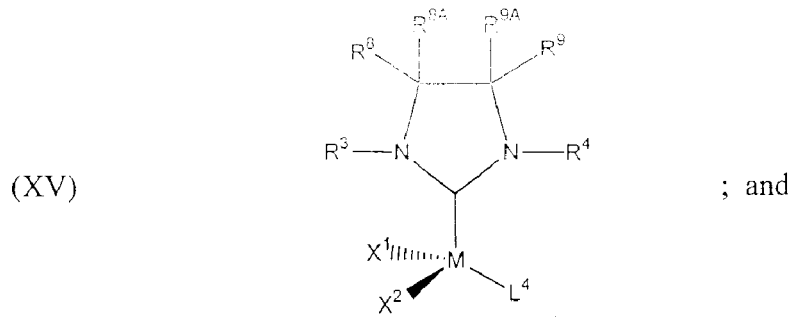
; and

Signed and Sealed this

Twenty-third Day of December, 2003

JAMES E. ROGAN
*Director of the United States Patent and Trademark Office*